(12) United States Patent
Sommer et al.

(10) Patent No.: US 8,639,340 B2
(45) Date of Patent: Jan. 28, 2014

(54) IMPLANTABLE MEDICAL LEAD CONNECTOR SLEEVES

(75) Inventors: John L. Sommer, Coon Rapids, MN (US); Douglas S. Hine, Forest Lake, MN (US); Douglas N. Hess, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1552 days.

(21) Appl. No.: 10/635,166

(22) Filed: Aug. 6, 2003

(65) Prior Publication Data
US 2005/0033371 A1 Feb. 10, 2005

(51) Int. Cl.
*A61N 1/375* (2006.01)

(52) U.S. Cl.
USPC .......................................................... 607/37

(58) Field of Classification Search
USPC ............... 607/36–38, 119; 439/909, 322, 312
See application file for complete search history.

(56) References Cited

U.S. PATENT DOCUMENTS

| 4,248,237 | A |   | 2/1981  | Kenny |   |
|---|---|---|---|---|---|
| 4,540,236 | A |   | 9/1985  | Peers-Trevarton |   |
| 4,583,543 | A | * | 4/1986  | Peers-Trevarton | 607/1 |
| 4,740,170 | A |   | 4/1988  | Lee et al. | 439/177 |
| 4,934,367 | A |   | 6/1990  | Daglow et al. |   |
| 5,007,435 | A | * | 4/1991  | Doan et al. | 607/119 |
| 5,007,864 | A |   | 4/1991  | Stutz, Jr. | 439/651 |
| 5,257,622 | A |   | 11/1993 | Hooper et al. |   |
| 5,366,494 | A |   | 11/1994 | Holleman et al. | 607/119 |
| 5,439,391 | A |   | 8/1995  | McEtchin et al. | 439/518 |
| 5,730,628 | A | * | 3/1998  | Hawkins | 439/843 |
| 5,766,042 | A |   | 6/1998  | Ries et al. | 439/668 |
| 5,769,671 | A | * | 6/1998  | Lim | 439/843 |
| 6,029,089 | A | * | 2/2000  | Hawkins et al. | 607/37 |
| 6,327,502 | B1 | * | 12/2001 | Johansson et al. | 607/36 |
| 6,671,554 | B2 | * | 12/2003 | Gibson et al. | 607/37 |
| 6,705,900 | B2 | * | 3/2004  | Sommer et al. | 439/668 |
| 6,816,745 | B1 | * | 11/2004 | Brand et al. | 607/37 |
| 6,913,478 | B2 | * | 7/2005  | Lamirey | 439/259 |
| 6,915,169 | B2 | * | 7/2005  | Flynn et al. | 607/122 |
| 6,934,588 | B1 | * | 8/2005  | Brand et al. | 607/37 |
| 2002/0115343 | A1 |   | 8/2002  | Sommer et al. | 439/578 |
| 2003/0069625 | A1 |   | 4/2003  | Ley et al. | 607/122 |
| 2003/0073348 | A1 |   | 4/2003  | Ries et al. | 439/578 |

FOREIGN PATENT DOCUMENTS

| EP | 0 590 756 A2 | 4/1994 | ............ A61N 1/375 |
|---|---|---|---|
| WO | WO 00/11762 | 3/2000 | ............ H01R 25/00 |

OTHER PUBLICATIONS

Written Opinion from PCT/US2004/019265, 5 pages.

* cited by examiner

*Primary Examiner* — Niketa Patel
*Assistant Examiner* — Alyssa M Alter
(74) *Attorney, Agent, or Firm* — Reed A. Duthler; Stephen W. Bauer (57) ABSTRACT

A connector sleeve includes a lumen adapted to receive a medical lead connector wherein a retention element engages a retention edge formed at a distal end of a connector element included on the lead connector. The connector sleeve further includes a contact element adapted to electrically engage the lead connector element within the lumen and an external conductive surface electrically coupled to the contact element and adapted for electrical engagement within the connector bore of an implantable medical device.

16 Claims, 7 Drawing Sheets

IMPLANTABLE MEDICAL LEAD CONNECTOR SLEEVES

TECHNICAL FIELD

The invention relates to medical devices and, more particularly, to connector sleeves coupling implantable medical leads to implantable medical devices (IMDs).

BACKGROUND

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses via electrodes disposed on the leads. In addition, implantable leads are used in neurological devices such as deep-brain stimulation devices, and spinal cord stimulation devices. Leads are also used with a wide variety of other medical devices including, for example, devices that sense chemical conditions in a patient's blood, and implantable drug or beneficial agent dispensers or pumps. In short, medical leads can be used for sensing purposes, stimulation purposes, drug delivery, and so forth.

Medical leads include a lead body formed of an outer polymeric sheath encasing one or more insulated electrical conductors; the lead body extends from a connector, terminating a proximal end, to a distal end. A distal end of each conductor is coupled to one or more electrodes while a proximal end of each conductor is coupled to a contact of the connector that is in turn coupled to a connector port of an implantable medical device (IMD), which delivers pulses or shocks to a patient via the lead electrodes, or receives sensed signals from the electrodes.

IMDs often include one or more connector ports conforming to one or more connector standards, examples of such standards include the IS-1 standard for low voltage electrical coupling and the DF-1 standard for high voltage electrical coupling, both commonly used in implantable cardiac pacemakers and defibrillators. When a lead connector does not conform to a standard, a connector sleeve may be fitted over the lead connector in order to adapt the connector for coupling within a standard connector port of an IMD. In such a system, means to secure or retain the connector sleeve on the lead connector is a desirable feature.

BRIEF DESCRIPTION OF DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following description is exemplary in nature and is not intended to limit the scope, applicability, or configuration of the invention in any way. Rather, the following description provides a convenient illustration for implementing exemplary embodiments of the invention.

Figure 1:
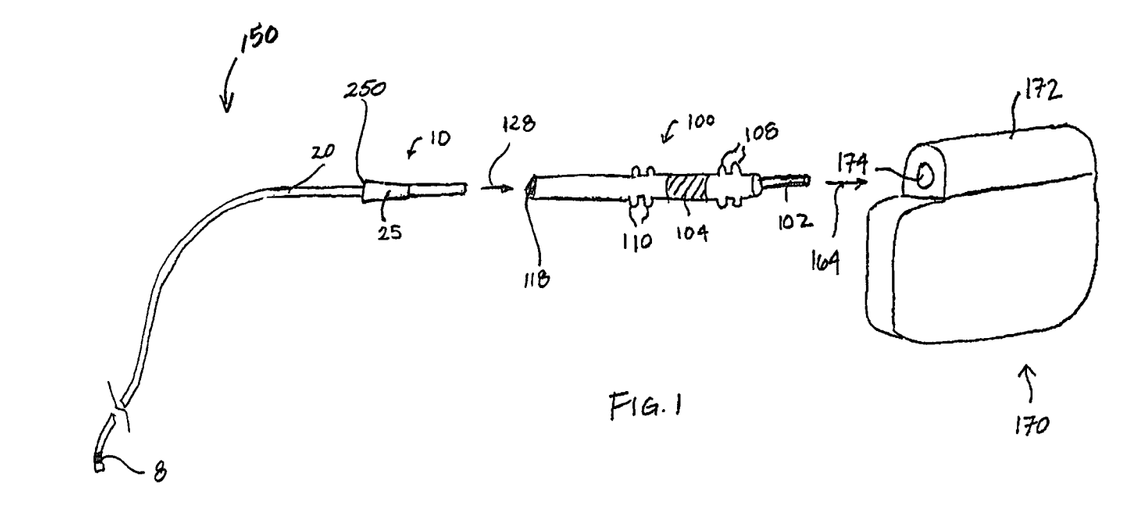
FIG. 1 is a schematic view of an implantable medical device system according to an embodiment of the present invention.

FIG. 1 is a schematic view of an implantable medical device system according to one embodiment of the present invention. FIG. 1 illustrates the medical system including an IMD 170, a medical electrical lead 150 and a connector sleeve 100 adapted to fit over a connector 10 terminating a proximal end of lead 150 in order to electrically couple a connector element 25 of lead connector 10 to IMD 170; connector element 25, coupled to an electrode 8 of lead 150 via an elongated insulated conductor 20, is electrically engaged within a lumen 118 of connector sleeve 100, when lead connector 10 is fully inserted within lumen 118, so that an exterior conductive surface 104 or 102 of sleeve 100 may be electrically coupled to IMD 170 within a port 174 of a connector header 172. In some embodiments according to the present invention, connector sleeve 100 and IMD port 174 may conform to an IMD connector standard, for example the IS-1 and the DF-1 connector standards commonly used in implantable cardiac pacemakers; FIG. 1 illustrates sleeve 100 generally conforming to the IS-1 standard including conductive surface 102 in the form of a terminal pin, conductive surface 104 in the form of a connector ring, a proximal set of sealing rings 108, and a distal set of sealing rings 110. Construction details and materials for conforming lead connectors and mating IMD connector headers are well known to those skilled in the art.

Figure 2A:
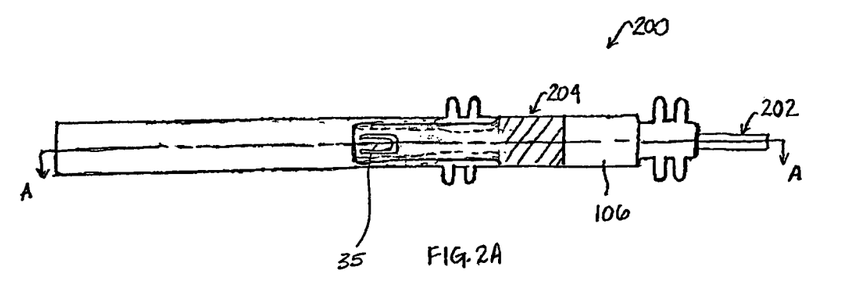
FIG. 2A is a plan view of a connector sleeve according to an embodiment of the present invention.
Figure 2B:
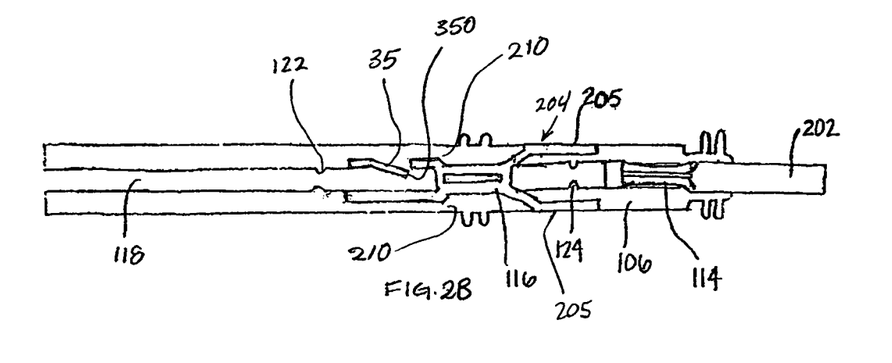
FIG. 2B is a section view of the connector sleeve shown in FIG. 2A.

As further illustrated in FIG. 1, according embodiments of the present invention, connector element 25 includes a retention edge 250 adapted to mate with a retention element (not shown) located within sleeve 100 in order to secure engagement of lead connector 10 within sleeve lumen 118. FIGS. 2A-B are a plan view and a section view through line A-A of a connector sleeve 200 according to an embodiment of the present invention wherein a lever retention element 35, including a leading edge 350, is incorporated mate with a retention edge of a lead connector element, for example edge 250 of connector element 25 illustrated in FIG. 1, in order to retain a lead connector, e.g. connector 10, which has been inserted into lumen 118 of sleeve 200. In the embodiment illustrated in FIGS. 2A-B, a connector ring 204 includes a conductive surface 205 and an portion extending within a sidewall 210 of sleeve 200, which includes an electrical contact 116 and retention element 35 positioned distal to contact 116. According to an embodiment of the present invention leading edge 350 of retention element 35 protrudes into lumen 118 and is deflected upward by a lead connector inserted within lumen 118 as will be further described in conjunction with FIGS. 2C-E. Electrical contact 116 may be a multi-beam spring contact, as illustrated, or any suitable electrical contact adapted to electrically engage a lead connector element, e.g. element 25 illustrated in FIG. 1, such as is known to those skilled in the art. FIG. 2B further illustrates a pin contact 202 including an electrical contact 114 within a sidewall 106 and a pair of internal sealing members 122 and 124 which serve to electrically isolate contacts 114 and 116; alternate embodiments include both contacts 116, 114, and both sealing members 122, 124, just contact 116 and sealing member 122, or just contact 114 and either sealing member 122 or 124, depending on the type of lead connector which sleeve couples to an IMD. In further alternate embodiments of sleeves, wherein a lead connector includes external sealing rings, according to configurations known to those skilled in the art, sealing members 122,124 are not included.

Figure 2C:
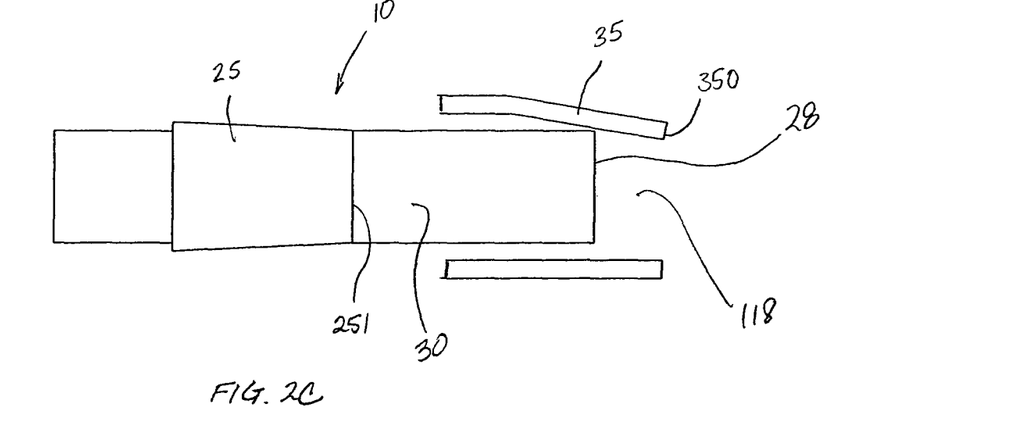
FIGS. 2C-E are partial section view schematics of a lead connector inserted into a portion of the connector sleeve shown in FIGS. 2A-B.
Figure 2D:
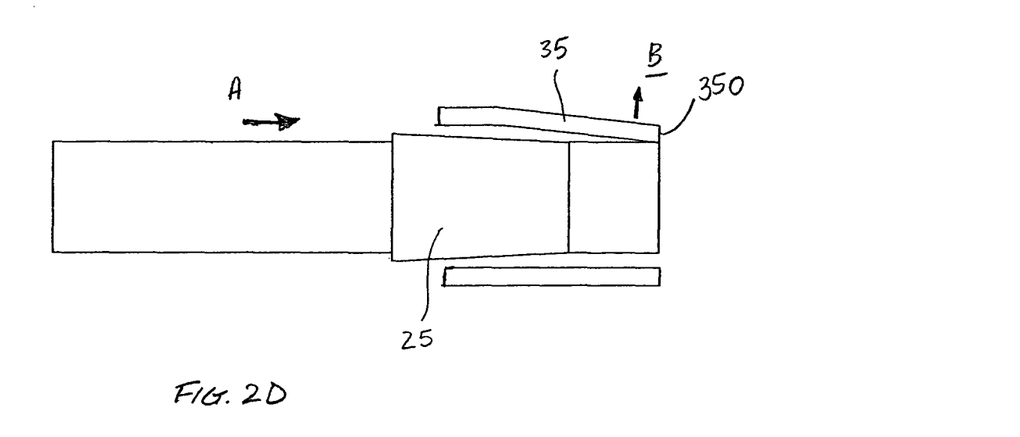
Figure 2E:
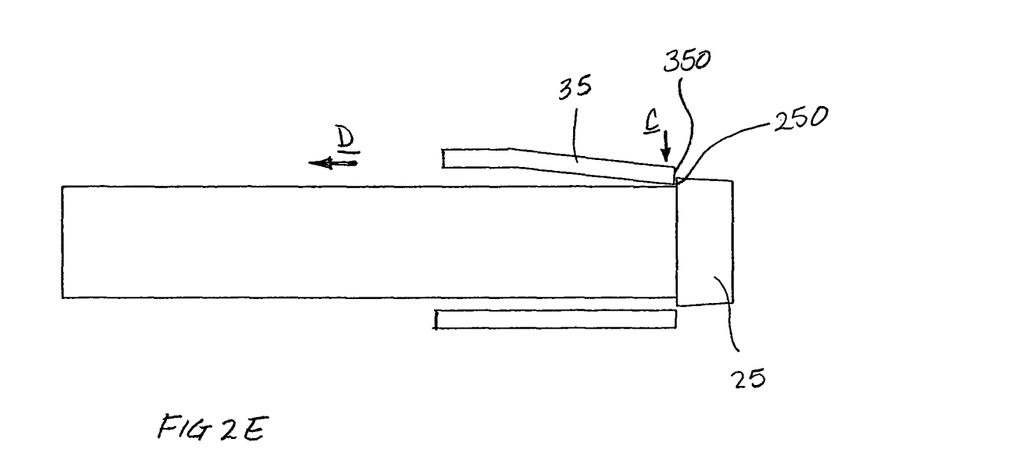

FIGS. 2C-E are partial section view schematics illustrating means by which lead connector 10 interacts with lever retention element 35 having resilient properties according to embodiments of the present invention. A proximal end 28 of lead connector 10 is inserted within lumen 118, per arrow A, thereby deflecting leading edge 350 of lever 35 from an initial position according to arrow B; after connector element 25 passes under lever 35, leading edge 350 rebounds per arrow C to abut edge 250 of connector element thus retaining lead connector 10 within lumen 118 and preventing withdrawal of lead per arrow D.

In alternate embodiments according to the present invention, leading edge 350 of lever retention element 35 is initially positioned so as not to protrude into lumen 118 and is pressed inward following insertion of lead connector 10 into lumen; in this case lever 85 is plastically deformed to retain lead connector.

Figure 3A:
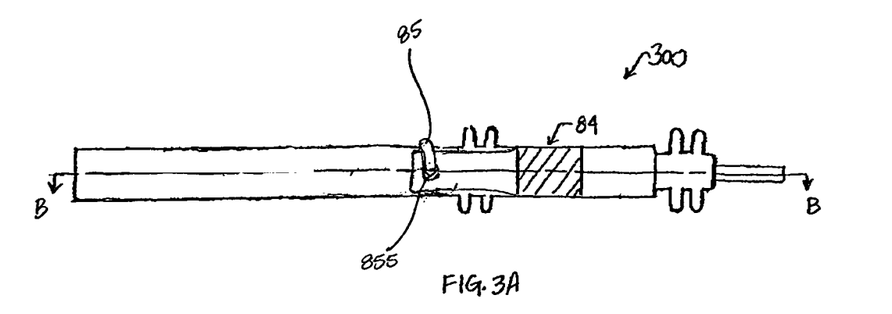
FIG. 3A is a plan view of a connector sleeve according to another embodiment of the present invention.
Figure 3B:
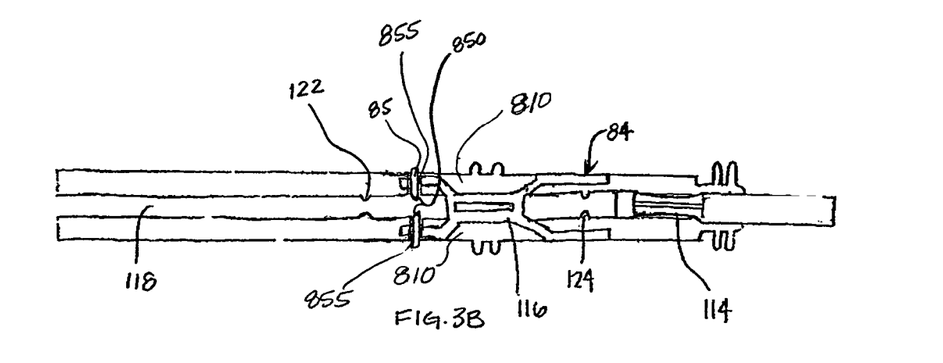
FIG. 3B is a sectional view of the connector sleeve show in FIG. 3A.
Figures 3C, 3D:
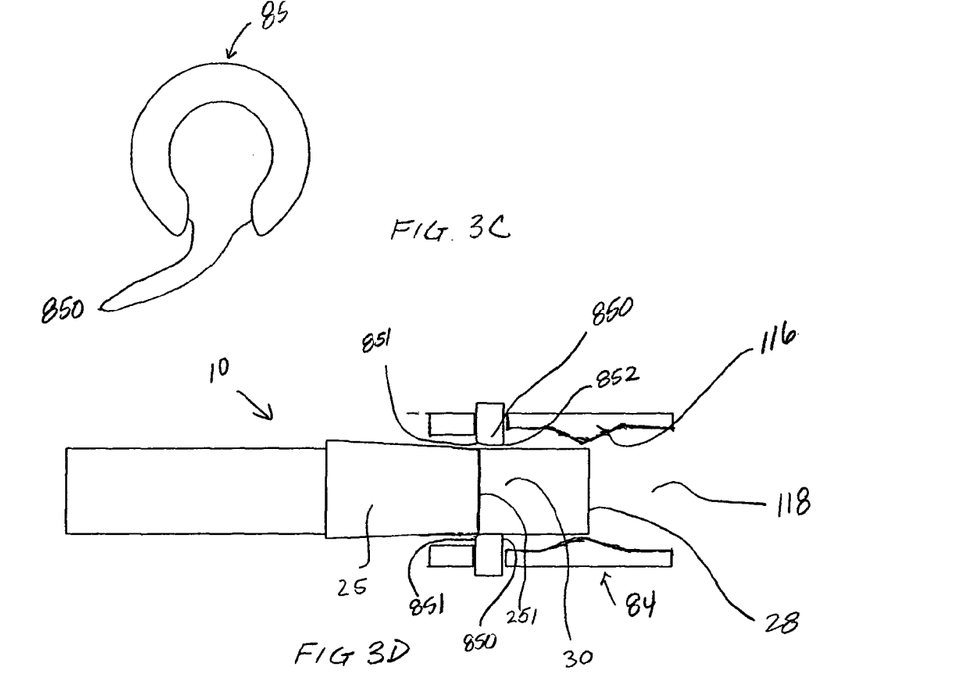
FIG. 3C is a front view of a retention element included in the connector sleeve shown in FIGS. 3A-B.
FIGS. 3D-F are partial section views of a lead connector inserted into a portion of the connector sleeve shown in FIGS. 3A-B.

FIGS. 3A-B are a plan view and a sectional view through line B-B of a connector sleeve 300 according to another embodiment of the present invention. FIGS. 3A-B illustrate sleeve 300 including passages 855 through a sidewall 810, which allow opposing ends 850 of a clip ring retention element 85 to protrude into lumen 118. FIG. 3C is a front view of clip ring retention element 85. According to embodiments of the present invention opposing ends 850 of retention element 85 are deflected outward by a lead connector inserted within lumen 118 as will be further described in conjunction with FIGS. 3D-F. According to the embodiment shown in FIGS. 3A-B, a portion of a connector ring 84 extends within sidewall 810 incorporating passages 855.

Figure 3E:
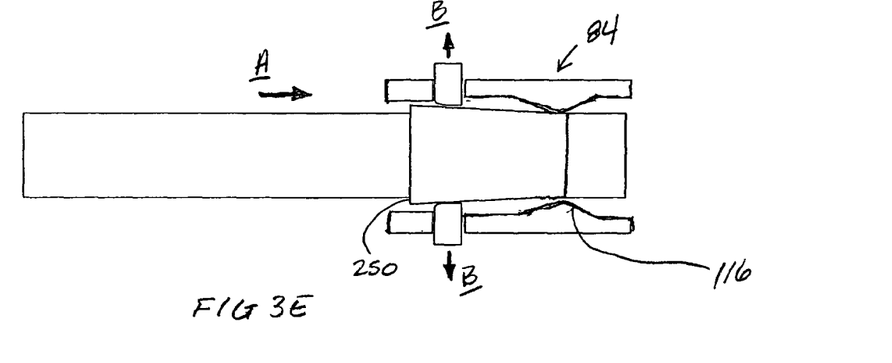
Figure 3F:
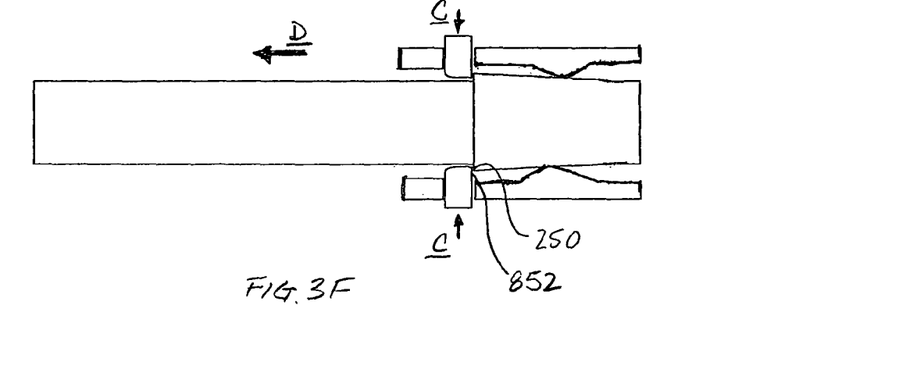

FIGS. 3D-F are partial section view schematics illustrating means by which a lead connector 110 interacts with clip ring retention element 85 having resilient properties according to embodiments of the present invention. A proximal end 28 of lead connector 10 is inserted within lumen 118, per arrow A, thereby deflecting opposing ends 850 of clip ring 85 from initial positions according to arrows B; after connector element 25 passes through ends 850, ends 850 rebound per arrow C to abut edge 250 of connector element thus retaining lead connector 10 within lumen 118 and preventing withdrawal of lead per arrow D. As is further illustrated in FIGS. 3D-F distal edges 851 of ends 850 are tapered to facilitate passage of lead connector 10 through lumen 118 while proximal edges 852 of ends 850 are blunt to assure that lead cannot be removed via arrow D; according to an alternate embodiment proximal and distal edges of ends 850 are similar, either both tapered or both blunt.

In alternate embodiments according to the present invention, opposing ends 850 of clip ring retention element 85 are initially positioned so as not to protrude into lumen 118 and are pressed inward following insertion of lead connector 10 into lumen; in this case clip ring 85 is plastically deformed to retain lead connector.

Referring to FIGS. 2C and 3D, according to some embodiments of the present invention a leading edge 251 of connector element 25 is substantially flush with an adjacent portion 30 of connector 10 to facilitate insertion of connector element 25 through retention elements 35 and 85. Additional embodiments further define connector element 25 as tapering from a first diameter at leading edge 251 to a second diameter, which is greater than the first diameter at retention edge 250.

Figure 4A:
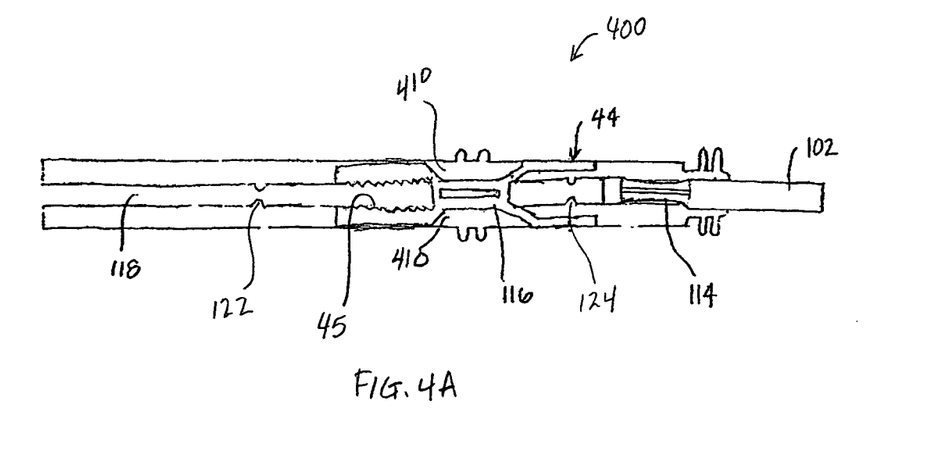
FIG. 4A is a section view of a connector sleeve according to yet another embodiment of the present invention.
Figure 4B:
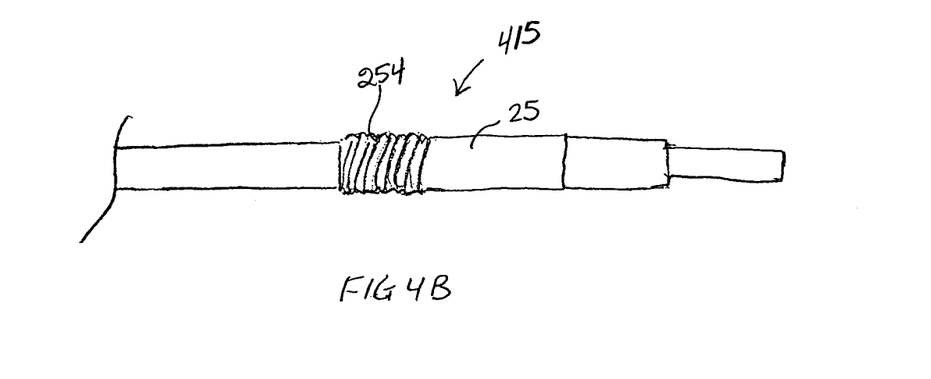
FIG. 4B is a plan view of a lead connector for combination with the connector sleeve shown in FIG. 4A.

FIG. 4A is a section view of a connector sleeve 400 according to yet another embodiment of the present invention and FIG. 4B is a plan view of a lead connector 415 for combination connector sleeve 400. FIG. 4A illustrates sleeve 400 including a female thread retention element 45 formed along a surface of lumen 118 to engage a retention edge formed as a mating male thread 254 of connector element 25 illustrated in FIG. 4B when connector 410 is inserted within sleeve 400. As further illustrated in FIG. 4A, connector ring 44 includes a portion extending within a sidewall 410 that includes contact 116 and retention element 45 according to one embodiment.

Figure 5A:
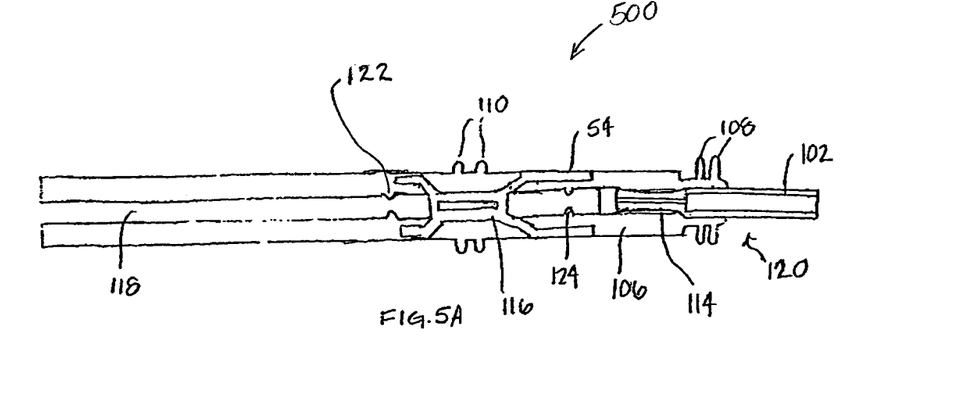
FIG. 5A is a section view of a connector sleeve according to yet another embodiment of the present invention.
Figure 5B:
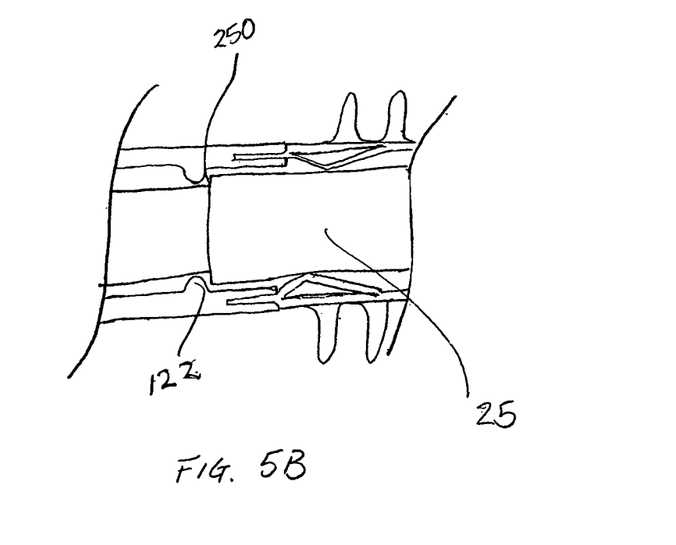
FIG. 5B is a partial section view of a lead connector inserted within a portion of the connector sleeve shown in FIG. 5A.

FIG. 5A is a section view of a connector sleeve 500 according to yet another embodiment of the present invention and FIG. 5B is a partial section view of lead connector 10 inserted within a portion of connector sleeve 500. According to the embodiment illustrated by FIGS. 5A-B internal sealing member 122 serves as a resilient retention member interfacing with retention edge 250 of connector member 25 in order to retain a lead connector, e.g. connector 10, which has been inserted into lumen 118 of sleeve 500 in a manner similar to that described for resilient lever and clip ring elements illustrated in FIGS. 2A-E and FIGS. 3A-F.

Methods for constructing connector sleeves described herein are taught in commonly assigned, co-pending U.S. Pat. application, publication number 2002/0115343.

In the foregoing specification, the invention has been described with reference to specific embodiments. However, it may be appreciated that various modifications and changes can be made without departing from the scope of the invention as set forth in the appended claims. Accordingly, the specification and figures are to be regarded as illustrative rather than as restrictive, and all such modifications are intended to be included within the scope of the present invention.

What is claimed is:

1. A medical system comprising:
   an implantable medical device including a connector bore;
   an electrical lead connector including a connector element;
      the connector element comprising a portion defining a retention edge with an engagement surface extending laterally to a centerline axis of the connector element; and
   a connector sleeve including
      a lumen adapted to receive the lead connector,
      a contact element within the connector sleeve lumen adapted to electrically engage the connector element,
      a retention element extending into the sleeve lumen, the retention element deflectable during insertion of the electrical lead connector into the connector sleeve lumen and redeploying to its initial position to mechanically engage the retention edge surface of the connector element portion and retain the connector element within the connector sleeve lumen and an external conductive surface electrically coupled to the contact element and adapted for electrical engagement within the connector bore of the implantable medical device.

2. The medical system of claim 1, wherein the connector sleeve further includes a sidewall and the retention element comprises a deflectable clip ring having opposing ends protruding into the lumen through the sidewall to mechanically abut the retention edge surface of the connector element within the lumen of the connector sleeve.

3. The medical system of claim 1, wherein the retention element of the connector sleeve and the contact element of the connector sleeve are integrally formed.

4. A medical electrical lead adaptor assembly, comprising:
a lead connector adapted to be coupled to a medical electrical lead and having a connector element comprising a portion defining a retention edge with an engagement surface extending laterally to a centerline axis of the connector element;
a connector sleeve having a lumen adapted to receive a lead connector;
a contact element within the sleeve lumen adapted to electrically engage a connector element of the lead connector
a retention element extending into the sleeve lumen and deflecting during insertion of the lead connector into the connector sleeve lumen and redeploying to its initial position to mechanically engage the retention edge surface of the connector element portion and retain the lead connector within the connector sleeve lumen; and
an external conductive surface on the connector sleeve electrically coupled to the contact element and adapted for electrical connection to an implantable medical device.

5. The medical lead adaptor assembly of claim 4, wherein the connector sleeve further comprises a sidewall and wherein the retention element comprises a deflectable clip ring having opposing ends protruding into the lumen through the sidewall.

6. The medical lead adaptor assembly of claim 4, wherein the retention element and the contact element are integrally formed.

7. A medical system comprising:
an implantable medical device including a connector bore;
an electrical lead connector including a connector element; the connector element comprising a portion defining a laterally extending retention edge; and
a connector sleeve including
a lumen adapted to receive the lead connector,
a contact element within the connector sleeve lumen adapted to electrically engage the connector element,
a retention element extending into the sleeve lumen, the retention element deflectable during insertion of the electrical lead connector into the connector sleeve lumen and redeploying to its initial position to mechanically engage the retention edge of the connector element portion and retain the connector element within the connector sleeve lumen and
an external conductive surface electrically coupled to the contact element and adapted for electrical engagement within the connector bore of the implantable medical device.

8. The medical system of claim 7, wherein the connector sleeve further includes a sidewall and the retention element comprises a deflectable lever formed in the sidewall to mechanically abut the retention edge surface of the connector element within the lumen of the connector sleeve.

9. The medical system of claim 7, wherein the connector sleeve further includes a sidewall and the retention element comprises a deflectable clip ring having opposing ends protruding into the lumen through the sidewall to mechanically abut the retention edge surface of the connector element within the lumen of the connector sleeve.

10. The medical system of claim 7, wherein the retention element comprises a resilient protrusion.

11. The medical system of claim 7, wherein the retention element of the connector sleeve and the contact element of the connector sleeve are formed integrally with one another.

12. A medical electrical lead adaptor assembly, comprising:
a lead connector adapted to be coupled to a medical electrical lead and having a connector element comprising a laterally extending retention edge;
a connector sleeve having a lumen adapted to receive a lead connector;
a contact element within the sleeve lumen adapted to electrically engage a connector element of the lead connector
a retention element extending into the sleeve lumen and deflecting during insertion of the lead connector into the connector sleeve lumen and redeploying to its initial position to mechanically engage the retention edge of the connector element portion and retain the lead connector within the connector sleeve lumen; and
an external conductive surface on the connector sleeve electrically coupled to the contact element and adapted for electrical connection to an implantable medical device.

13. The medical electrical lead adaptor assembly of claim 12, wherein the connector sleeve further comprises a sidewall and wherein the retention element comprises a deflectable lever formed in the sidewall to mechanically abut the retention edge surface of the connector element portion.

14. The medical lead adaptor assembly of claim 12, wherein the connector sleeve further comprises a sidewall and wherein the retention element comprises a deflectable clip ring having opposing ends protruding into the lumen through the sidewall.

15. The medical lead adaptor assembly of claim 13, wherein the retention element comprises a resilient protrusion.

16. The medical lead adaptor assembly of claim 13, wherein the retention element and the contact element are formed integrally with one another.

* * * * *